US009488598B2

(12) United States Patent
Kim et al.

(10) Patent No.: US 9,488,598 B2
(45) Date of Patent: Nov. 8, 2016

(54) INSPECTING APPARATUS FOR INSPECTING A MULTILAYER STRUCTURE

(71) Applicant: Samsung Display Co., Ltd., Yongin, Gyeonggi-Do (KR)

(72) Inventors: Wal Jun Kim, Hwaseong-si (KR); Seung Young Baeck, Cheonan-si (KR)

(73) Assignee: SAMSUNG DISPLAY CO., LTD. (KR)

( * ) Notice: Subject to any disclaimer, the term of this patent is extended or adjusted under 35 U.S.C. 154(b) by 81 days.

(21) Appl. No.: 14/530,952

(22) Filed: Nov. 3, 2014

(65) Prior Publication Data
US 2015/0346107 A1 Dec. 3, 2015

(30) Foreign Application Priority Data

Jun. 2, 2014 (KR) .................. 10-2014-0066941

(51) Int. Cl.
*G01N 21/84* (2006.01)
*G01N 21/94* (2006.01)
*G01N 21/88* (2006.01)
*G01N 21/958* (2006.01)

(52) U.S. Cl.
CPC ........ *G01N 21/958* (2013.01); *G01N 21/8422* (2013.01); *G01N 21/84* (2013.01); *G01N 21/88* (2013.01); *G01N 21/94* (2013.01); *G01N 2021/8438* (2013.01); *G01N 2201/068* (2013.01)

(58) Field of Classification Search
USPC ..................... 356/237.1–241.6, 242.1–243.8, 356/426–431, 600–640
See application file for complete search history.

(56) References Cited

U.S. PATENT DOCUMENTS

| | | | | |
|---|---|---|---|---|
| 3,652,863 A * | 3/1972 | Gaskell | ................ | G01N 21/896 250/224 |
| 4,808,813 A * | 2/1989 | Champetier | ........... | G01N 21/94 250/223 B |
| 5,172,421 A * | 12/1992 | Nakamura | ............. | G01M 11/35 250/559.08 |
| 5,198,335 A * | 3/1993 | Sekikawa | ................ | C12Q 1/32 422/417 |
| 5,355,213 A * | 10/1994 | Dotan | ................ | G01N 21/8806 356/124 |
| 5,790,247 A * | 8/1998 | Henley | ................ | G01N 21/958 356/237.1 |
| 6,404,489 B1 * | 6/2002 | Yu | ........................ | G01N 21/958 356/239.1 |
| 6,587,711 B1 * | 7/2003 | Alfano | ................. | A61B 5/0068 600/410 |
| 7,292,332 B2 * | 11/2007 | Gerstner | .............. | G01N 21/896 356/239.1 |
| 7,307,714 B2 * | 12/2007 | Cyr | ..................... | G01N 21/958 356/237.1 |

(Continued)

FOREIGN PATENT DOCUMENTS

| | | |
|---|---|---|
| JP | 2000-230910 A | 8/2000 |
| JP | 2005-069989 A | 3/2005 |
| JP | 2006-226801 A | 8/2006 |
| KR | 1020010076687 A | 8/2001 |
| KR | 1020060098690 A | 9/2006 |

(Continued)

*Primary Examiner* — Tri Ton
*Assistant Examiner* — Jarreas C Underwood
(74) *Attorney, Agent, or Firm* — Cantor Colburn LLP

(57) ABSTRACT

An inspecting apparatus includes: a stage including a top surface on which a multilayer structure comprising a first layer and a second layer is placed; a first light irradiation unit which faces a first side surface of the multilayer structure and provides light to a first side surface of the first layer or a first side surface of the second layer; an image capture unit which is on the stage, receives scattered light from the multilayer structure and generates image information of the multilayer structure from the received scattered light, and a control unit which detects foreign body information of the multilayer structure based on the image information of the multilayer structure. The scattered light comprises the light which is provided from the first light irradiation unit and is scattered within the multilayer structure.

20 Claims, 12 Drawing Sheets

(56) References Cited

U.S. PATENT DOCUMENTS

| | | | |
|---|---|---|---|
| 8,736,581 B2* | 5/2014 | Han | G06F 3/0412 178/18.09 |
| 9,157,869 B2* | 10/2015 | Ortner | G01N 21/9505 |
| 2012/0095305 A1* | 4/2012 | Wang | A61B 5/0075 600/323 |
| 2013/0010216 A1* | 1/2013 | Kang | G06F 3/0412 349/12 |

FOREIGN PATENT DOCUMENTS

| | | |
|---|---|---|
| KR | 1020080067137 A | 7/2008 |
| KR | 1020110103683 A | 9/2011 |
| KR | 1020130014191 A | 2/2013 |
| KR | 1020130028458 A | 3/2013 |
| KR | 1020130078721 A | 7/2013 |
| KR | 1020130078799 A | 7/2013 |
| KR | 1020130086801 A | 8/2013 |

* cited by examiner

INSPECTING APPARATUS FOR INSPECTING A MULTILAYER STRUCTURE

This application claims priority to Korean Patent Application No. 10-2014-0066941 filed on Jun. 2, 2014, and all the benefits accruing therefrom under 35 U.S.C. §119, the disclosure of which is incorporated herein by reference in its entirety.

BACKGROUND

1. Field

The invention relates to an inspecting apparatus.

2. Description of the Related Art

The development of semiconductor technology is creating many demands for smaller and lighter displays. Examples of such displays include a liquid crystal display ("LCD") and an organic light-emitting diode display ("OLED"). LCDs and OLEDs are being widely used because they can be made to be smaller, lighter and consume less power.

To reduce the overall thickness of a display, elements such as a window, a touch panel, etc. are attached directly to a display panel using a transparent adhesive (e.g., resin) in a modularization process. Accordingly, thinner displays are being released onto the market.

However, foreign bodies are likely to be inserted into a multilayer structure in the process of forming the multilayer structure in which the elements such as the window, the touch panel, etc. are attached to the display panel using, e.g., resin. Therefore, after the above elements are attached to the display panel, an inspection process is performed to determine whether a foreign body exists between the display panel and the above elements.

SUMMARY

A conventional inspecting apparatus captures an image of a multilayer structure in which display elements such as a window, a touch panel, etc. are attached to a display panel using, e.g., resin, using a camera and detects whether a defect exists in the captured image.

Therefore, the conventional inspecting apparatus can detect the presence of a foreign body in the multilayer structure but cannot identify whether the foreign body exists on a surface of the multilayer structure or within the multilayer structure. It is also difficult for the conventional inspecting apparatus to identify in which layer of the multilayer structure the foreign body exists.

One or more exemplary embodiment of the invention provides an inspecting apparatus which can accurately detect at which position and in which layer of a multilayer structure a defect or a foreign body exists.

Exemplary embodiments of the invention are not restricted to those set forth herein. The above and other features of the invention will become more apparent to one of ordinary skill in the art to which the invention pertains by referencing the detailed description of the invention given below.

According to an exemplary embodiment of the invention, there is provided an inspecting apparatus. The inspecting apparatus includes a stage including a top surface on which a multilayer structure including a first layer and a second layer is placed, a first light irradiation unit which faces a first side surface of the multilayer structure and provides light to a first side surface of the first layer or a first side surface of the second layer, an image capture unit which is on the stage, receives scattered light from the multilayer structure and generates image information of the multilayer structure from the received scattered light, where the scattered light includes the light which is provided from the first light irradiation unit and is scattered within the multilayer structure, and a control unit which detects foreign body information of the multilayer structure based on the image information.

According to another exemplary embodiment of the invention, there is provided an inspecting apparatus. The inspecting apparatus includes a stage including a top surface on which a multilayer structure including a first layer and a second layer is placed, a first light irradiation unit which faces a first side surface of the multilayer structure, provides light of a first color to a first side surface of the first layer, and provides light of a second color to a first side surface of the second layer, an image capture unit which is on the stage, receives scattered light from the multilayer structure and generates image information of the multilayer structure from the scattered light, where the scattered light includes light of the first color or the light of the second color which is provided from the first light irradiation unit and is scattered within the multilayer structure, and a control unit which detects foreign body information of the multilayer structure based on the image information.

According to another exemplary embodiment of the invention, there is provided an inspecting apparatus. The inspecting apparatus includes a stage including a top surface on which a multilayer structure including a first layer and a second layer is placed, a first light irradiation unit which faces a first side surface of the multilayer structure and provides light of a first color to a first side surface of the first layer, a second light irradiation unit which faces a second side surface of the multilayer structure different from the first side surface and provides light of a second color to a second side surface of the second layer, an image capture unit which is located on the stage, receives scattered light from the multilayer structure and generates image information of the multilayer structure from the received scattered light, where the scattered light includes the light of the first color or the light of the second color which is provided from the first light irradiation unit or the second light irradiation unit, respectively, and is scattered within the multilayer structure, and a control unit which detects foreign body information of the multilayer structure based on the image information.

Other features and exemplary embodiments will be apparent from the following detailed description, the drawings and the claims.

BRIEF DESCRIPTION OF THE DRAWINGS

The above and other features of the invention will become more apparent by describing in detail exemplary embodiments thereof with reference to the attached drawings, in which.

DETAILED DESCRIPTION

Figure 1A:
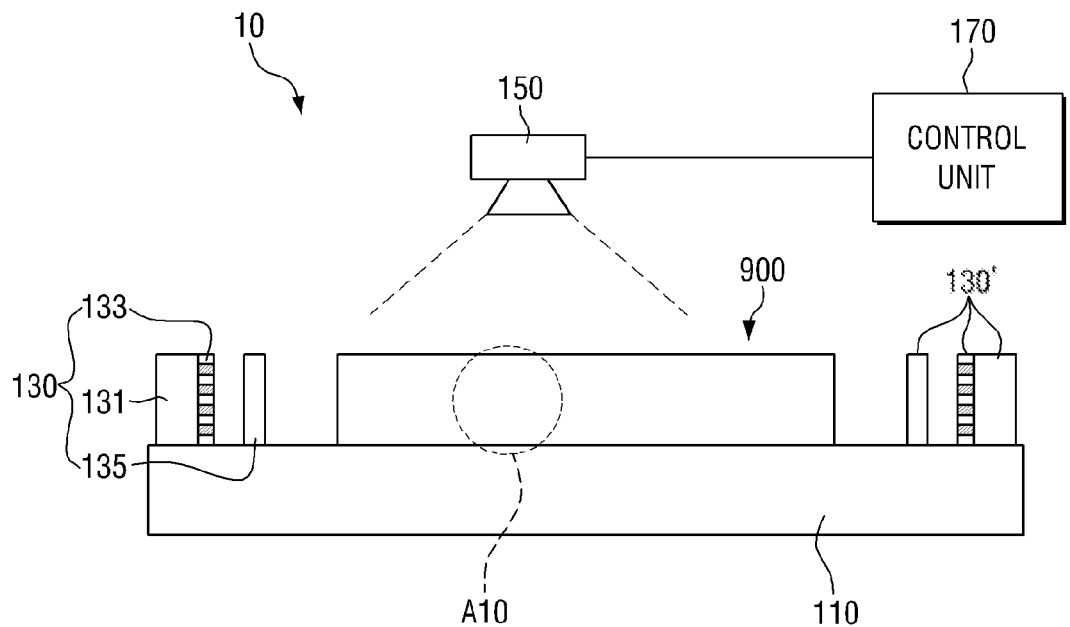
FIGS. 1A and 1B are cross-sectional views illustrating an exemplary embodiment of an inspecting apparatus according to the invention.

The invention will now be described more fully hereinafter with reference to the accompanying drawings, in which exemplary embodiments of the invention are shown. This invention may, however, be embodied in different forms and should not be construed as limited to the exemplary embodiments set forth herein. Rather, these exemplary embodiments are provided so that this disclosure will be thorough and complete, and will filly convey the scope of the invention to those skilled in the art.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, connected may refer to elements being physically and/or electrically connected to each other. The same reference numbers indicate the same components throughout the specification. In the attached figures, the thickness of layers and regions is exaggerated for clarity.

It will be understood that, although the terms first, second, third, etc., may be used herein to describe various elements, these elements should not be limited by these terms. These terms are only used to distinguish one element from another element. Thus, a first element discussed below could be termed a second element without departing from the teachings of the invention.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "below," "lower (or bottom)," "above," "upper (or top)" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the invention will be described with reference to the attached drawings.

Figure 1B:
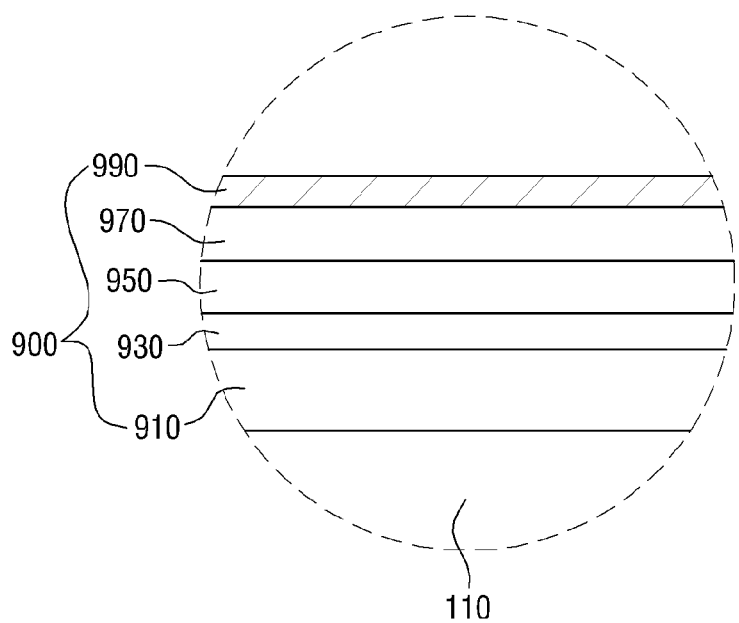

FIGS. 1A and 1B are cross-sectional views illustrating an exemplary embodiment of an inspecting apparatus 10 according to the invention. FIG. 1B is an enlarged view of portion A10 of FIG. 1A.

Referring to FIGS. 1A and 1B, the inspecting apparatus 10 may include a stage 110 which supports a multilayer structure 900 (e.g., an object to be inspected) placed on a top surface thereof, a first light irradiation unit 130, an image capture unit 150 and a control unit 170.

The multilayer structure 900 is an object to be inspected by the inspecting apparatus 10 and may include a first layer and a second layer. Throughout the specification, the multilayer structure 900 including a display panel 910, a polarizer 930 located on the display panel 910, a resin layer 950 located on the polarizer 930, a touch panel 970 located on the resin layer 950, and a protective film 990 located on the touch panel 970 will be described as an example, but the invention is not limited thereto. The first layer may be any one of the polarizer 930, the resin layer 950, the touch panel 970 and the protective film 990 included in the multilayer structure 900, and the second layer may be another one (which is different from that of the first layer) of the polarizer 930, the resin layer 950, the touch panel 970 and the protective film 990 included in the multilayer structure 900. However, this is merely an example used for ease of description, and the invention is not limited to this example.

The first light irradiation unit 130 provides light to a side surface of the multilayer structure 900. Specifically, the first light irradiation unit 130 provides light to side surfaces of two or more of the polarizer 930, the resin layer 950, the touch panel 970 and the protective film 990. The first light irradiation unit 130 may be placed to face a first side surface 900a of the multilayer structure 900. The first light irradiation unit 130 may be located on the stage 110 as illustrated in the drawing, but the invention is not limited thereto.

The first light irradiation unit 130 may include a first light source unit 131, a first light transmission adjustment unit 133 and a first lens unit 135.

The first light source 131 generates and outputs light toward the first side surface 900a of the multilayer structure 900. In some exemplary embodiments, the first light source unit 131 may include a laser or light-emitting diode ("LED") that generates and emits light.

The first light transmission adjustment unit 133 may transmit or block light emitted from the first light source unit 131. The first light transmission adjustment unit 133 may be located between the first side surface 900a of the multilayer structure 900 and the first light source unit 131.

The first light transmission adjustment unit 133 may include shutters that can be opened and shut.

Figure 2:
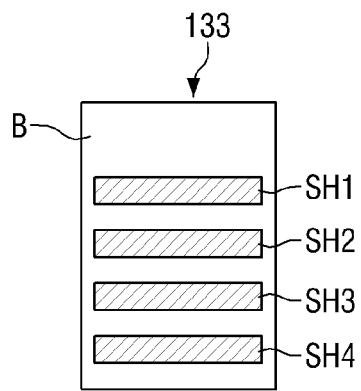
FIGS. 2 and 3 are front and side views, respectively, illustrating an exemplary embodiment of a first light transmission adjustment unit of FIG. 1.
Figure 3:
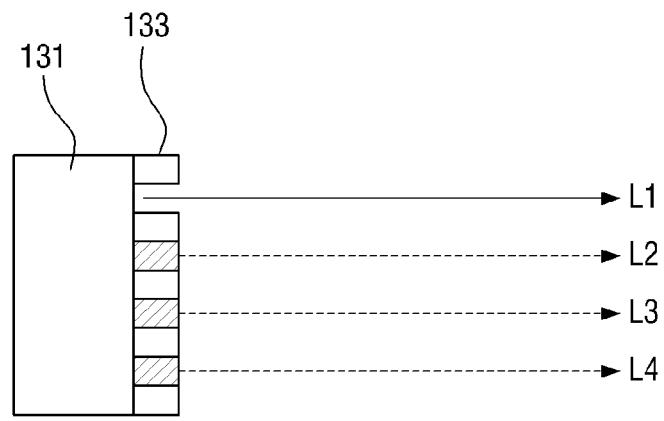

FIGS. 2 and 3 are front and side view, respectively, illustrating the first light transmission adjustment unit 133 of FIG. 1. More specifically, FIG. 2 is a front view of the first light transmission adjustment unit 133 of FIG. 1, and FIG. 3 is a diagram illustrating the operation of the first light transmission adjustment unit 133 of FIG. 1.

Referring to FIGS. 1 and 2, the first light transmission adjustment unit 133 may include a body B, and shutters SH1 through SH4 which are included or defined in the body B and can be opened and shut.

There is no limit to the number of the shutters SH1 through SH4. In the drawings, four shutters SH1 through SH4 are illustrated. However, this is merely an example, and the number of the shutters SH1 through SH4 can be changed appropriately. In some exemplary embodiments, the number of the shutters SH1 through SH4 may be equal to the number of layers included in the multilayer structure 900. However, the invention is not limited thereto, and the number of the shutters SH1 through SH4 can be changed appropriately if necessary.

In some exemplary embodiments, the shutters SH1 through SH4 may be located at positions respectively corresponding to the layers of the multilayer structure 900. In an exemplary embodiment, for example, if the layers of the multilayer structure 900 are the protective film 990, the touch panel 970, the resin layer 950 and the polarizer 930, the shutters SH1 through SH4 may be located at positions corresponding to the protective film 990, the touch panel 970, the resin layer 950 and the polarizer 930, respectively. In other words, referring to FIGS. 1A and 1B, the first shutter SH1 may be located at substantially the same level as (or in substantially the same plane with) the protective film 990, and the second shutter SH2 may be located at substantially the same level as the touch panel 970. In addition, the third shutter SH3 may be located at substantially the same level as the resin layer 950, and the fourth shutter SH4 may be located at substantially the same level as the polarizer 930.

Each of the shutters SH1 through SH4 may open or shut independently to selectively transmit or block light emitted from the first light source unit 131.

In some exemplary embodiments, each of the shutters SH1 through SH4 may be implemented as a microshutter which is a kind of microelectromechanical system ("MEMS"). The microshutter has the property of being transformed by an electrostatic force generated from an electric field applied thereto. The first light transmission adjustment unit 133 may directly transmit or block light according to the operation of the microshutter by taking advantage of the transformation property of the microshutter.

Referring to FIGS. 1 through 3, the shutters SH1 through SH4 of the first light transmission adjustment unit 133 may open and shut individually. The shutters SH1 through SH4 may open at different times. In other words, when any one of the shutters SH1 through SH4 opens, the other shutters may remain shut. In an exemplary embodiment, for example, as illustrated in FIG. 3, while the first shutter SH1 is open, the other shutters (e.g., the second shutter SH2, the third shutter SH3 and the fourth shutter SH4) excluding the first shutter SH1 may remain shut. A portion L1 of light emitted from the first light source unit 131 may transmit (shown as a solid line arrow) through the open first shutter SH1 (shown as unshaded in FIG. 3), and the other portions L2, L3 and L4 of the light may be blocked (shown as a dotted line arrow) by the shut second, third and fourth shutters SH2, SH3 and SH4 (shown as shaded in FIG. 3), respectively. Likewise, although not illustrated in the drawings, while the second shutter SH2 is open, the first, third and fourth shutters SH1, SH3 and SH4 may remain shut. Another portion L2 of the light emitted from the first light source unit 131 may transmit through the open second shutter SH2, and the other portions of the light L1, L3 and L4 may be blocked by the shut first, third and fourth shutters SH1, SH3 and SH4, respectively. For ease of description, of the light emitted from the first light source unit 131, light that transmits through the open first shutter SH1, light that transmits through the open second shutter SH2, light that transmits through the open third shutter SH3 and light that transmits through the open fourth shutter SH4 will be referred to as first light L1, second light L2, third light L3 and fourth light L4, respectively.

The opening and shutting operation of each of the shutters SH1 through SH4 may be controlled by the control unit 170 (refer to FIG. 1A).

Referring back to FIG. 1A, the first lens unit 135 may be located between the first light transmission adjustment unit 133 and the first side surface 900a of the multilayer structure 900. The first lens unit 135 converts light, which transmits through the first light transmission adjustment unit 133 among the light emitted from the first light source unit 131, into sheet light.

Figure 4:
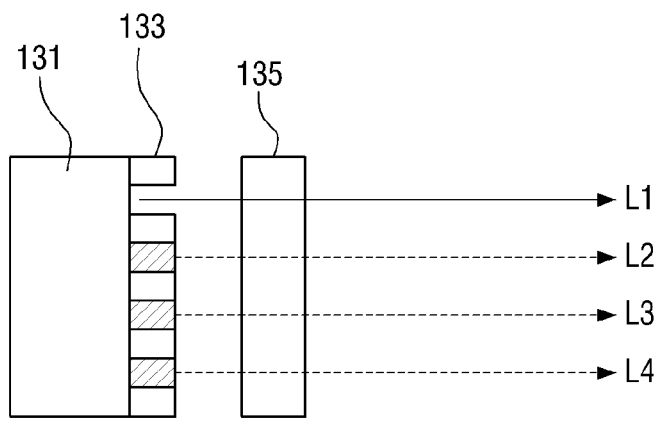
FIGS. 4 and 5 are diagrams illustrating the function of an exemplary embodiment of a first lens unit of FIG. 1.
Figure 5:
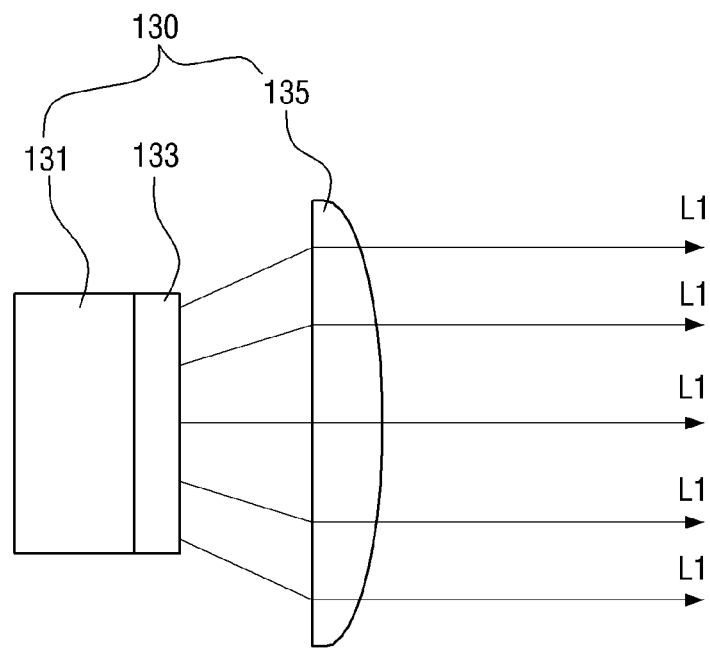

FIGS. 4 and 5 are diagrams illustrating the function of an exemplary embodiment of a first lens unit 135 of FIG. 1. Specifically, FIG. 4 is a diagram illustrating the form of light viewed from the side, and FIG. 5 is a diagram illustrating the form of light viewed from above (e.g., a top plan view of) the first lens unit 135. Referring to FIGS. 4 and 5, the first lens unit 135 may diffuse light, which transmits through the first light transmission adjustment unit 133 among light emitted from the first light source unit 131, in the form of sheet light or flat light. That is, when viewed from the side, light (L1) that transmits through the first lens unit 135 may be in the form of parallel light as illustrated in FIG. 4. When viewed from above, the light (L1) that transmits through the first lens unit 135 may be in the form of sheet light or flat light as illustrated in FIG. 5. In some exemplary embodiments, the first lens unit 135 may include a cylindrical lens. The first lens unit 135 can also include other lenses capable of diffusing light.

Referring back to FIG. 1, the image capture unit 150 may be located above the stage 110.

The image capture unit 150 obtains image information by receiving light (or scattered light) generated when light irradiated from the first light irradiation unit 130 is scattered by a foreign body existing within the multilayer structure 900. In some exemplary embodiments, the image capture unit 150 may include, but not limited to, a charge-coupled device ("CCD") or a complementary metal oxide semiconductor ("CMOS") capable of obtaining image information (or an image) by receiving scattered light.

The control unit 170 detects foreign body information of the multilayer structure 900 based on image information obtained by the image capture unit 150. In some exemplary embodiments, the control unit 170 may detect the foreign body information based on at least one of color, chroma, and light and shade included in the image information. In an exemplary embodiment, for example, a portion corresponding to a foreign body existing within the multilayer structure 900 may appear relatively bright due to scattered light. Here, the control unit 170 may detect the foreign body information by analyzing the light and shade of the image information (or the image). However, this is merely an example, and a method by which the control unit 170 detects the foreign body information is not limited to this example.

The control unit 170 may control the overall operation of the inspecting apparatus 10. In an exemplary embodiment, for example, the control unit 170 may further control the opening and shutting operation of each of the shutters SH1 through SH4.

The inspecting apparatus 10 may further include a second light irradiation unit 130'. The second light irradiation unit 130' may be placed to face side surfaces excluding the first side surface 900a from among the four side surfaces of the multilayer structure 900. In an exemplary embodiment, the second light irradiation unit 130' may be placed to face a second side surface 900b of the multilayer structure 900 as illustrated in the drawing, but the invention is not limited thereto. The structure of the second light irradiation unit 130' may be identical to that of the first light irradiation unit 130. Although not illustrated in the drawing, the inspecting apparatus 10 may further include a light irradiation unit which faces side surfaces of the multilayer structure 900 excluding the first side surface 900a and the second side surface 900b, from among side surfaces in the top plan view.

Figure 6:
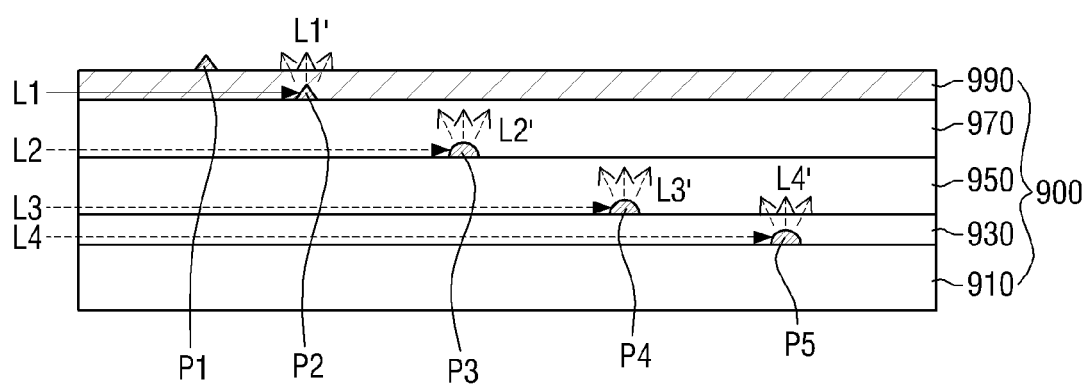
FIG. 6 is a diagram illustrating an exemplary embodiment of a process of detecting foreign bodies using the inspecting apparatus of FIG. 1.

FIG. 6 is a diagram illustrating an exemplary embodiment of a process of detecting foreign bodies using the inspecting apparatus 10 of FIG. 1.

A multilayer structure 900 including first through fifth foreign bodies P1 through P5 will now be described as an example with reference to FIGS. 1 through 6. The first foreign body P1 may be viewable without assistance, since the first foreign body P1 is disposed outside the multilayer structure 900.

Referring to FIGS. 1 through 6, the second foreign body P2 may be detected as follows. The inspecting apparatus 10 drives the first light source unit 131 to emit light. The first light L1 is shown as a solid line arrow and second through fourth lights L2 through L4 are shown as dotted line arrows relating to the description in detecting the second foreign body P2. Then, the inspecting apparatus 10 opens the first shutter SH1 of the first light transmission adjustment unit 133 and keeps the second shutter SH2, the third shutter SH3 and the fourth shutter SH4 shut. Accordingly, of the light emitted from the first light source unit 131, only the first light L1 transmits through the first light transmission adjustment unit 133. Then, the first light L1 transmits through the first lens unit 135. As the transmitted light passes through the first lens unit 135, the first light L1 is transformed into sheet light and is incident accordingly upon a side surface of the protective film 990 which corresponds to the first shutter SH1. The first light L1 is scattered by the second foreign body P2 located between the touch panel 970 and the protective film 990 to generate first scattered light L1'. The image capture unit 150 receives the first scattered light L1' and obtains image information. The control unit 170 detects the second foreign body P2 by analyzing the image information obtained by the image capture unit 150. In addition, since the control unit 170 can control the opening and shutting operation of each of the shutters SH1 through SH4 of the first light transmission adjustment unit 133, the control unit 170 can detect the presence of the second foreign body P2 in the protective film 990 or between the protective film 990 and the touch panel 970. The first foreign body P1 and the second foreign body P2 can be removed when the protective film 990 is stripped off during a subsequent manufacturing process of a display including the multilayer structure 900. Consequently, despite the presence of the second foreign body P2, the control unit 170 may not determine the second foreign body P2 to be a foreign body defect.

The third foreign body P3 may be detected as follows. Although not illustrated in the drawings, the inspecting apparatus 10 drives the first light source unit 131 to emit light. Then, the inspecting apparatus 10 opens the second shutter SH2 of the first light transmission adjustment unit 133 and keeps the first shutter SH1, the third shutter SH3 and the fourth shutter SH4 shut. Accordingly, of the light emitted from the first light source unit 131, only the second light L2 transmits through the first light transmission adjustment unit 133. Then, the second light L2 transmits through the first lens unit 135. As the transmitted light passes through the first lens unit 135, the second light L2 is transformed into sheet light and is incident accordingly upon a side surface of the touch panel 970 which corresponds to the second shutter SH2. The second light L2 is scattered by the third foreign body P3 located between the touch panel 970 and the resin layer 950 to generate second scattered light L2'. The image capture unit 150 receives the second scattered light L2' and obtains image information. The control unit 170 detects the third foreign body P3 by analyzing the image information obtained by the image capture unit 150. In addition, since the control unit 170 can control the opening and shutting operation of each of the shutters SH1 through SH4 of the first light transmission adjustment unit 133, the control unit 170 can detect the presence of the third foreign body P3 in the touch panel 970 or between the touch panel 970 and the resin layer 950. The third foreign body P3 actually exists within the multilayer structure 900, that is, not exposed to outside the multilayer structure 900. Consequently, the control unit 170 may determine that the third foreign body P3 exists within the multilayer structure 900 and that a foreign body defect exists in the multilayer structure 900 based on the position of the third foreign body P3.

The fourth foreign body P4 may also be detected as described above. Although not illustrated in the drawings, when the inspecting apparatus 10 provides the third light L3 to a side surface of the resin layer 950 by opening the third shutter SH3 and shutting the first shutter SH1, the second shutter SH2 and the fourth shutter SH4, the third light L3 is scattered by the fourth foreign body P4 to generate third scattered light L3'. Then, the image capture unit 150 obtains image information from the third scattered light L3'. By analyzing the image information, the control unit 170 may determine that the fourth foreign body P4 exists in the resin layer 950 or between the resin layer 950 and the polarizer 930 and consequently determine that a foreign body defect exists within the multilayer structure 900.

For the fifth foreign body P5, although not illustrated in the drawings, when the inspecting apparatus 10 provides the fourth light L4 to the polarizer 930 by opening the fourth shutter SH4 and shutting the first shutter SH1, the second shutter SH2 and the third shutter SH3, the fourth light L4 is scattered by the fifth foreign body P5 to generate fourth scattered light L4'. Then, the image capture unit 150 obtains image information from the fourth scattered light L4'. By analyzing the image information, the control unit 170 may determine that the fifth foreign body P5 exists in the polarizer 930 or between the polarizer 930 and the display panel 910 and consequently determine that a foreign body defect exists within the multilayer structure 900.

According to the exemplary embodiment of the invention, not only the presence of a foreign body in the multilayer structure 900 but also the position of the foreign body can be detected. Therefore, accurate detection of whether a foreign body defect actually exists in the multilayer structure 900 and the position of the foreign body within the multilayer structure 900 is possible.

Figure 7A:
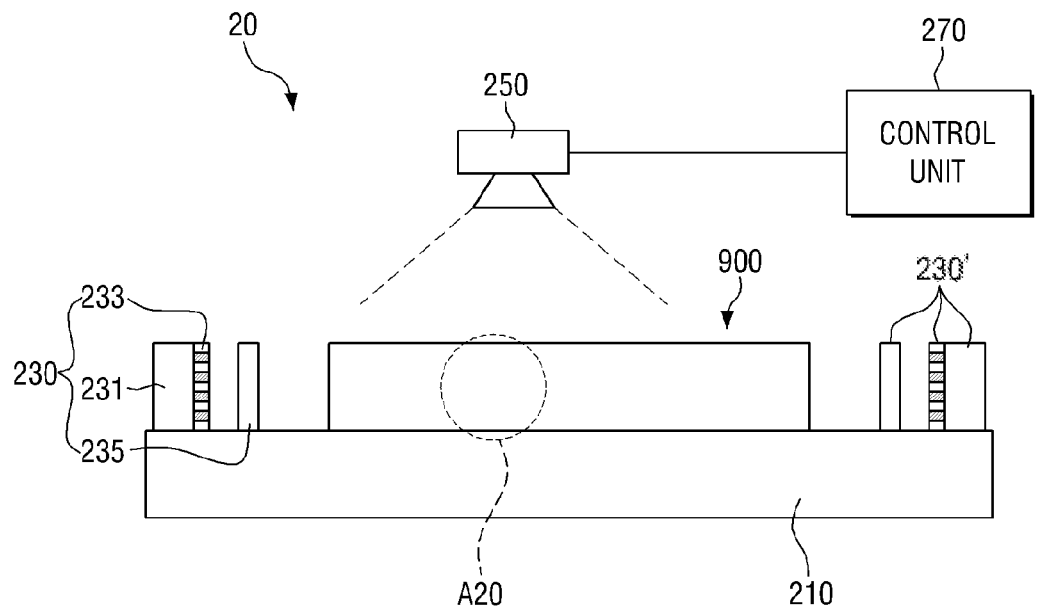
FIGS. 7A and 7B are cross-sectional views illustrating another exemplary embodiment of an inspecting apparatus according to the invention.
Figure 7B:
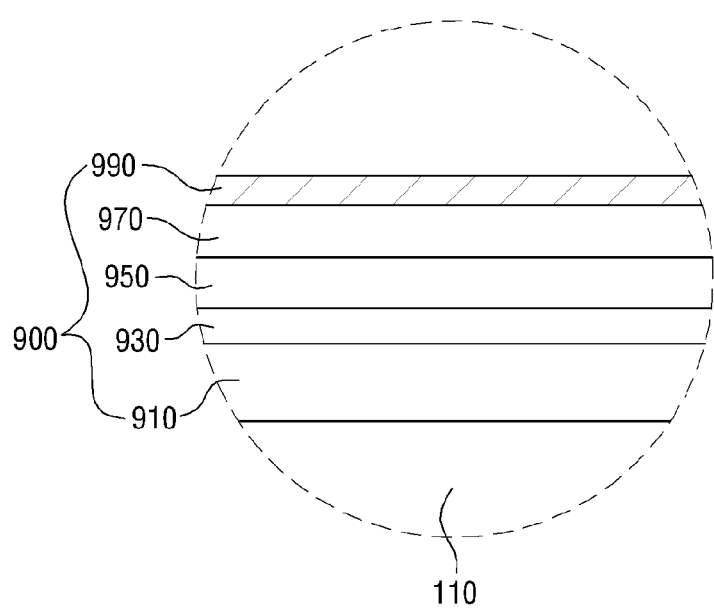

FIGS. 7A and 7B are cross-sectional views illustrating another exemplary embodiment an inspecting apparatus 20 according to the invention. FIG. 7B is an enlarged view of portion A20 of FIG. 7A.

Referring to FIGS. 7A and 7B, the inspecting apparatus 20 includes a stage 210 which supports a multilayer structure 900 (e.g., an object to be inspected) placed on a top surface thereof, a first light irradiation unit 230, an image capture unit 250 and a control unit 270.

The stage 210 supports the multilayer structure 900 placed on the top surface thereof.

The first light irradiation unit 230 provides light to a side surface of the multilayer structure 900. Specifically, the first light irradiation unit 230 provides light to side surfaces of two or more of a polarizer 930, a resin layer 950 a touch panel 970, and a protective film 990. Like the first light irradiation unit 130 described above with reference to FIG. 1, the first light irradiation unit 230 may be placed to face a first side surface 900a of the multilayer structure 900. The first light irradiation unit 230 may be located on the stage 210 as illustrated in the drawing, but the invention is not limited thereto.

The first light irradiation unit 230 may include a first light source unit 231, a first light conversion unit 233 and a first lens unit 235.

The first light source unit 231 generates and outputs light toward the first side surface 900a of the multilayer structure 900. In some exemplary embodiments, the first light source unit 231 may include a laser or LED that generates and emits light. In some exemplary embodiments, the color of light emitted from the first light source unit 231 may be white.

The first light conversion unit 233 converts the color of light emitted from the first light source unit 231. The first light conversion unit 233 may be located between the first side surface 900a of the multilayer structure 900 and the first light source unit 231.

The first light conversion unit 233 may include light conversion members which convert the color of incident light.

Figure 8:
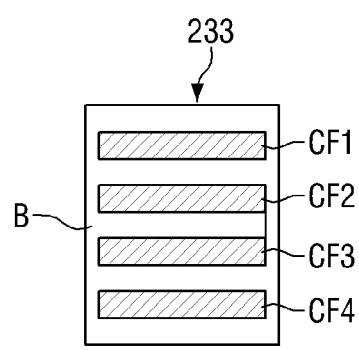
FIG. 8 is a front view of an exemplary embodiment of a first light conversion unit of FIG. 7.
Figure 9:
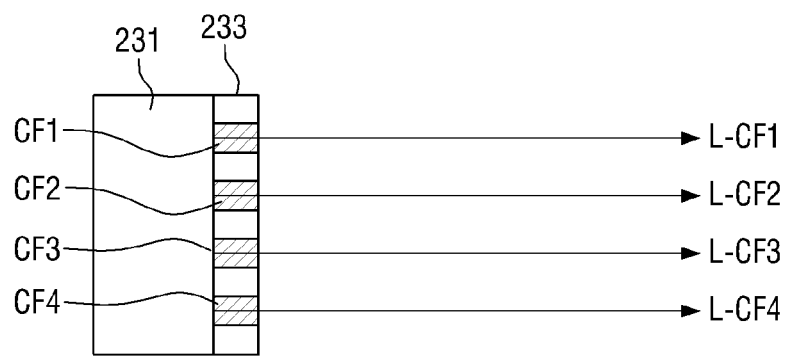
FIG. 9 is a side view illustrating the function of the first light conversion unit of FIG. 7.

FIGS. 8 and 9 are views illustrating an exemplary embodiment of the first light conversion unit 233 of FIG. 7. More specifically, FIG. 8 is a front view of the first light conversion unit 233 of FIG. 7, and FIG. 9 is a diagram illustrating the function of the first light conversion unit 233 of FIG. 7.

Referring to FIGS. 7 through 9, the first light conversion unit 233 may include a body B, and light conversion members CF1 through CF4 included in the body B.

There is no limit to the number of the light conversion members CF1 through CF4. In the drawings, four light conversion members CF1 through CF4 are illustrated. However, this is merely an example, and the number of the light conversion members CF1 through CF4 can be changed appropriately. In some exemplary embodiments, the number of the light conversion members CF1 through CF4 may be equal to the number of layers included in the multilayer structure 900. However, the invention is not limited thereto, and the number of the light conversion members CF1 through CF4 can be changed appropriately if necessary.

In some exemplary embodiments, the light conversion members CF1 through CF4 may be located at positions respectively corresponding to the layers of the multilayer structure 900. In an exemplary embodiment, for example, if the layers of the multilayer structure 900 are the protective film 990, the touch panel 970, the resin layer 950 and the polarizer 930, the light conversion members CF1 through CF4 may be located at positions corresponding to the protective film 990, the touch panel 970, the resin layer 950 and the polarizer 930, respectively. In other words, the first light conversion member CF1 may be located at substantially the same level as (or in substantially the same plane with) the protective film 990, and the second light conversion member CF2 may be located at substantially the same level as the touch panel 970. In addition, the third light conversion member CF3 may be located at substantially the same level as the resin layer 950, and the fourth light conversion member CF4 may be located at substantially the same level as the polarizer 930.

Each of the light conversion members CF1 through CF4 may convert the color of incident light into a different color. Assuming that a first color is red, a second color is green, a third color is blue and a fourth color is yellow, the first light conversion member CF1 may convert light emitted from the first light source unit 231 into light L-CF1 of the first color, e.g., red light, and the second light conversion member CF2 may convert the light emitted from the first light source unit 231 into light L-CF2 of the second color, e.g., green light. Likewise, the third light conversion member CF3 may convert the light emitted from the first light source unit 231 into light L-CF3 of the third color, e.g., blue light, and the fourth light conversion member CF4 may convert the light emitted from the first light source unit 231 into light L-CF4 of the fourth color, e.g., yellow light. The above colors are merely an example used for ease of description, and a color into which the color of light is converted by each light conversion member can be changed.

In some exemplary embodiments, each of the light conversion members CF1 through CF4 may be a color filter. In an exemplary embodiment, for example, the first light conversion member CF1 may be a red color filter, and the second light conversion member CF2 may be a green color filter. In addition, the third light conversion member CF3 may be a green color filter, and the fourth light conversion member CF4 may be a yellow color filter. However, this is merely an example, and any object can be used as each of the light conversion members CF1 through CF4 as long as it can convert the color of incident light. In an exemplary embodiment, for example, a wavelength conversion member including a fluorescent material can be applied to the invention as the light conversion member.

Referring to FIG. 7, the first lens unit 235 may be located between the first light conversion unit 233 and the first side surface 900a of the multilayer structure 900. The first lens unit 235 may convert light, which transmits through the first light conversion unit 233 among light emitted from the first light source unit 231, into sheet light. Other features of the first lens unit 235 are identical to those of the first lens unit 135 described above with reference to FIGS. 1, 4 and 5, and thus a description thereof will be omitted.

The image capture unit 250 may be located above the stage 210.

The image capture unit 250 obtains image information by receiving light (or scattered light) generated when light irradiated from the first light irradiation unit 230 is scattered by a foreign body existing within the multilayer structure 900. In some exemplary embodiments, the image capture unit 250 may obtain color image information (or a color image) by receiving scattered light. To this end, the image capture unit 250 may include, but not limited to, a CCD or a CMOS.

The control unit 270 detects foreign body information of the multilayer structure 900 based on image information obtained by the image capture unit 250. In some exemplary embodiments, the control unit 270 may detect the foreign body information based on at least one (in particular, color information) of color, chroma, and light and shade included in the image information. In addition, the control unit 270 may store the color information of light provided to each layer of the multilayer structure 900 and determine in which layer a foreign body exists based on the color information. Furthermore, the control unit 270 may control the overall operation of the inspecting apparatus 20.

The inspecting apparatus 20 may further include a second light irradiation unit 230'. The second light irradiation unit 230' may be placed to face side surfaces excluding the first side surface 900a from among the four side surfaces of the multilayer structure 900 in the top plan view. In an exemplary embodiment, the second light irradiation unit 230' may be placed to face a second side surface 900b of the multilayer structure 900 as illustrated in the drawing, but the invention is not limited thereto. The structure of the second light irradiation unit 230' may be identical to that of the first light irradiation unit 230. Although not illustrated in the drawing, the inspecting apparatus 20 may further include a light irradiation unit which faces side surfaces of the multilayer structure 900 excluding the first side surface 900a and the second side surface 900b, from among side surfaces in the top plan view.

Figure 10:
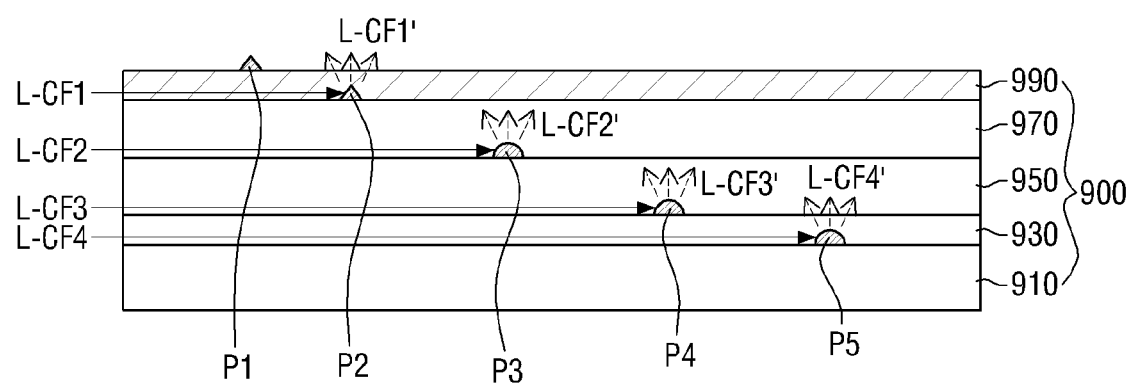
FIG. 10 is a diagram illustrating an exemplary embodiment of a process of detecting foreign bodies using the inspecting apparatus of FIG. 7.

FIG. 10 is a diagram illustrating an exemplary embodiment of a process of detecting foreign bodies using the inspecting apparatus 20 of FIG. 7.

A multilayer structure 900 including first through fifth foreign bodies P1 through P5 will now be described as an example with reference to FIGS. 7 through 10.

Referring to FIGS. 7 through 10, the inspecting apparatus 20 drives the first light source unit 231 to emit light. The light emitted from the first light source unit 231 is converted into the light L-CF1 of the first color, the light L-CF2 of the second color, the light L-CF3 of the third color and the light L-CF4 of the fourth color by passing through the first light conversion member CF1, the second light conversion member CF2, the third light conversion member CF3 and the fourth light conversion member CF4 of the first light conversion unit 233, respectively. Then, each of the light L-CF1 of the first color, the light L-CF2 of the second color, the light L-CF3 of the third color and the light L-CF4 of the fourth color transmits through the first lens unit 235. As each of the light L-CF1 of the first color, the light L-CF2 of the second color, the light L-CF3 of the third color and the light L-CF4 of the fourth color transmits through the first lens unit 235, the transmitted light transformed into sheet light and is incident accordingly upon respective side surfaces of the protective film 990, the touch panel 970, the resin layer 950 and the polarizer 930.

Once entering the multilayer structure 900, the light L-CF1 of the first color, the light L-CF2 of the second color, the light L-CF3 of the third color and the color L-CF4 of the fourth color are scattered by the second foreign body P2, the third foreign body P3, the fourth foreign body P4 and the fifth foreign body P5 to generate scattered light L-CF1' of the first color, scattered light L-CF2' of the second color, scattered light L-CF3' of the third color and scattered light L-CF4' of the fourth color, respectively. The image capture unit 250 obtains color image information by receiving the scattered light L-CF1' of the first color, the scattered light L-CF2' of the second color, the scattered light L-CF3' of the third color and the scattered light L-CF4' of the fourth color. The control unit 270 determines whether a foreign body exists within the multilayer structure 900 by analyzing the color image information obtained by the image capture unit 250.

In an example, the light L-CF1 of the first color may be red light, the light L-CF2 of the second color may be green light, the light L-CF3 of the third color may be blue light and the light L-CF4 of the fourth color may be yellow light. In the color image information obtained by the image capture unit 250, a portion corresponding to the second foreign body P2 may be displayed as a red dot, a portion corresponding to the third foreign body P3 may be displayed as a green dot, a portion corresponding to the fourth foreign body P4 may be displayed as a blue dot and a portion corresponding to the fifth foreign body P5 may be displayed as a yellow dot. By analyzing the color image information, the control unit 270 may detect whether the second foreign body P2, the third foreign body P3, the fourth foreign body P4 and the fifth foreign body P5 exist. In addition, the control unit 270 may detect in which layer of the multilayer structure 900 each of the second foreign body P2, the third foreign body P3, the fourth foreign body P4 and the fifth foreign body P5 is located based on the stored color information of light provided to each layer of the multilayer structure 900.

That is, since the control unit 270 can detect the presence and position of each of the foreign bodies P2 through P5, a single one inspection process can be used to detect whether defects actually exist within the multilayer structure 900.

In an exemplary embodiment, for example, the first foreign body P1 and the second foreign body P2 can be removed when the protective film 990 is stripped off during a subsequent manufacturing process of a display including the multilayer structure 900. Consequently, despite the presence of the second foreign body P2, the control unit 270 may not determine the second foreign body P2 to be a foreign body defect. On the other hand, the control unit 270 may determine the third foreign body P3, the fourth foreign body P4 and the fifth foreign body P5 to be foreign body defects.

According to the exemplary embodiment of the invention, not only the presence of a foreign body in the multilayer structure 900 but also the position of the foreign body can be detected. Therefore, accurate detection of whether a foreign body defect actually exists within the multilayer structure 900 and the position of the foreign body within the multilayer structure 900 is possible. Furthermore, since foreign body defects within the multilayer structure 900 can be detected through one single inspection process, an additional advantage of reducing inspection time can be provided.

Figure 11:
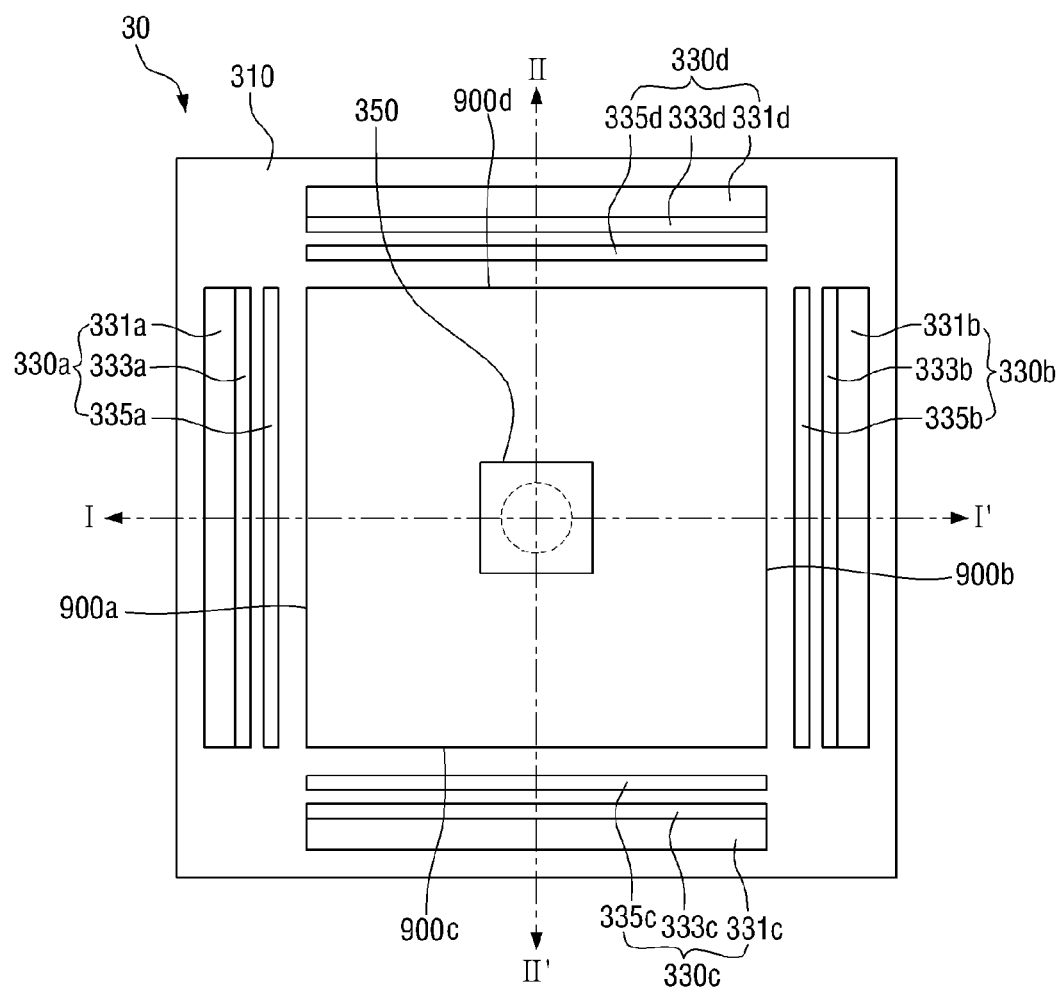
FIG. 11 is a plan view illustrating still another exemplary embodiment of an inspecting apparatus according to the invention.
Figure 12A:
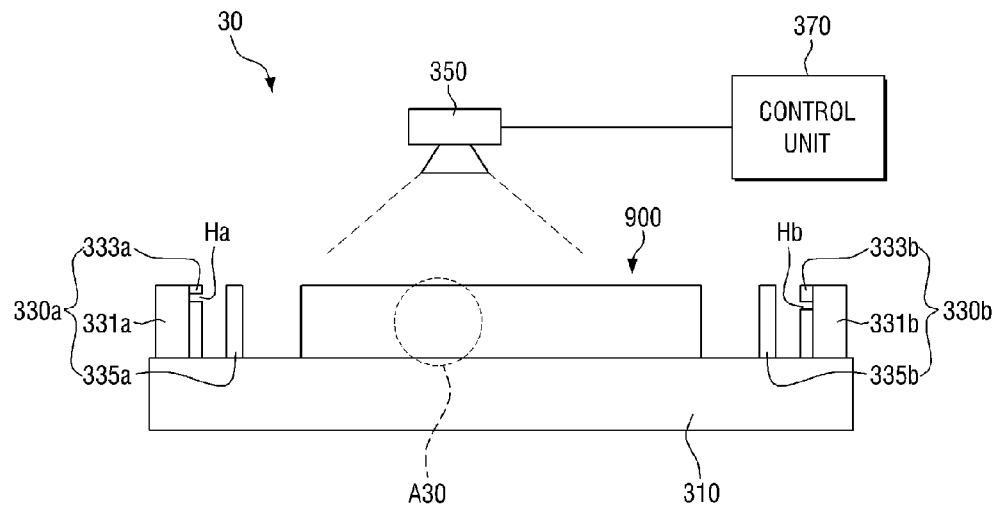
FIGS. 12A, 12B, 13A and 13B are cross-sectional views illustrating the inspecting apparatus of FIG. 11, and FIGS. 14 through 16 are diagrams illustrating an exemplary embodiment of a process of detecting foreign bodies using the inspecting apparatus of FIG. 11.
Figure 12B:
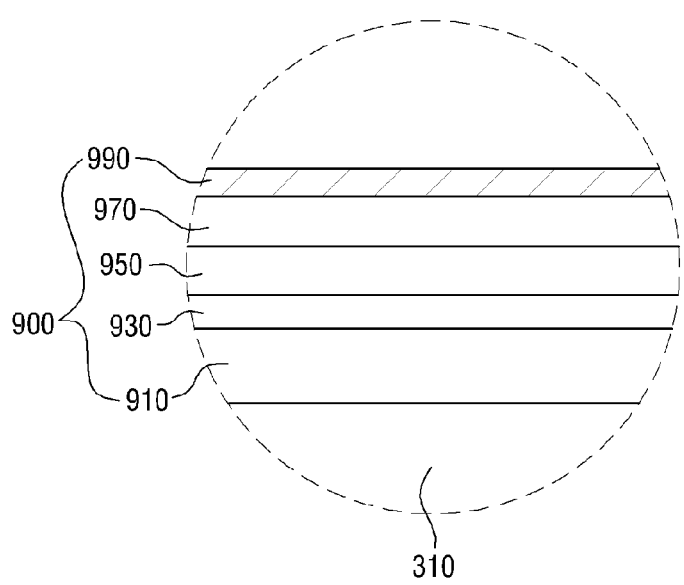
Figure 13A:
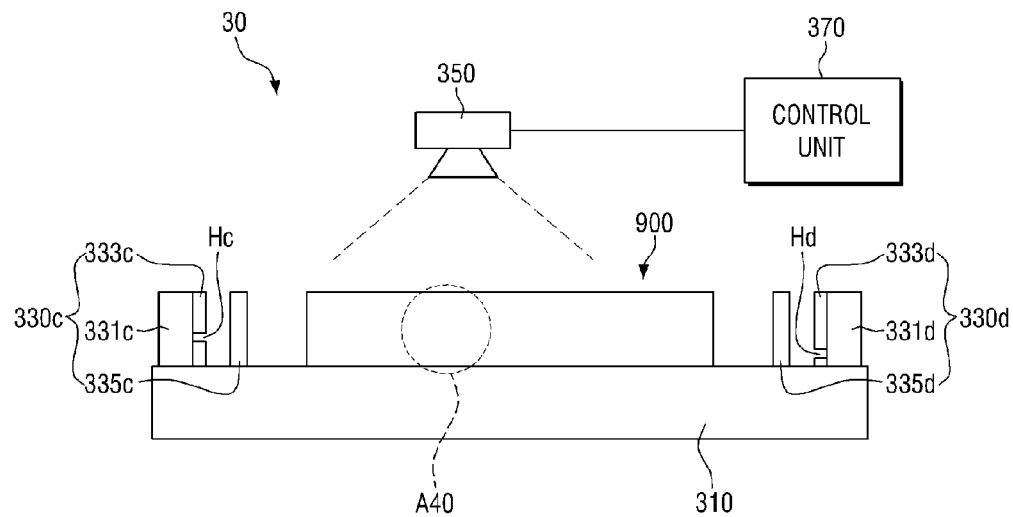
Figure 13B:
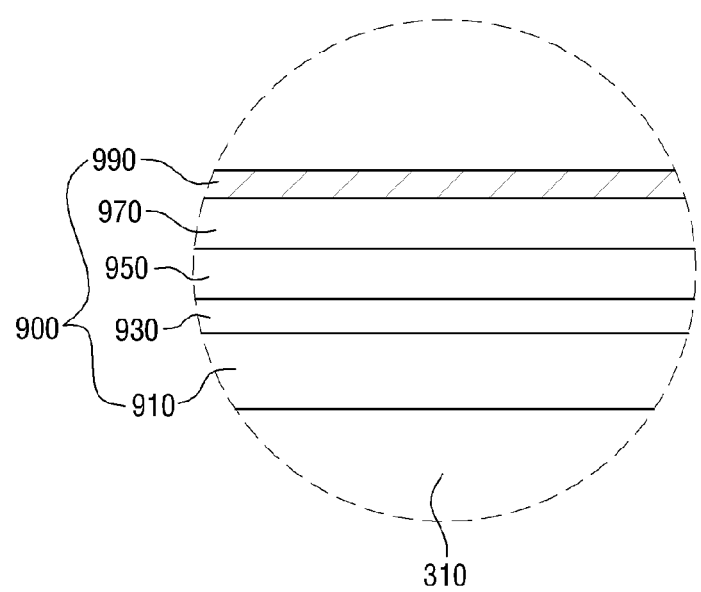

FIGS. 11 through 13 are diagrams illustrating still another exemplary embodiment of an inspecting apparatus 30 according to the invention. Specifically, FIG. 11 is a plan view of the inspecting apparatus 30, FIGS. 12A and 12B are cross-sectional views of the inspecting apparatus 30 taken along the line I-I' of FIG. 11, and FIGS. 13A and 13B are cross-sectional views of the inspecting apparatus 30 taken along the line II-II' of FIG. 11. FIG. 12B is an enlarged view of portion A30 of FIG. 12A, and FIG. 13B is an enlarged view of portion A40 of FIG. 13A.

Referring to FIGS. 11 through 13, the inspecting apparatus 30 may include a stage 310 which supports a multilayer structure 900 (e.g., an object to be inspected) placed on a top surface thereof, a first light irradiation unit 330a, a second light irradiation unit 330b, an image capture unit 350 and a control unit 370 and may further include at least any one of a third light irradiation unit 330c and a fourth light irradiation unit 330d. For ease of description, the inspecting apparatus 30 further including the third light irradiation unit 330c and the fourth light irradiation unit 330d will be described as an example.

The stage 310 supports the multilayer structure 900 placed on the top surface thereof.

The first light irradiation unit 330a provides light to a first side surface 900a of the multilayer structure 900. The first light irradiation unit 330a provides light to a side surface of any one of a polarizer 930, a resin layer 950, a touch panel 970, and a protective film 990. Like the first light irradiation unit 130 described above with reference to FIG. 1, the first light irradiation unit 330a may be placed to face the first side surface 900a of the multilayer structure 900. The first light irradiation unit 330a may be located on the stage 310 as illustrated in the drawings, but the invention is not limited thereto.

The first light irradiation unit 330a may include a first light source unit 331a, a first light transmission adjustment unit 333a and a first lens unit 335a.

The first light source unit 331a generates and outputs light of a first color toward the first side surface 900a of the multilayer structure 900. In some exemplary embodiments, the first light source unit 331a may include a laser or LED that generates and emits light.

The first light transmission adjustment unit 333a transmits only part of the light of the first color emitted from the first light source unit 331a. The first light transmission adjustment unit 333a may be located between the first side surface 900a of the multilayer structure 900 and the first light source unit 331a.

The first light transmission adjustment unit 333a may include a first hole Ha defined therein, and the first hole Ha may be located at a position corresponding to the protective film 990 of the multilayer structure 900. That is, light emitted from the first light source unit 331a may pass through the first hole Ha of the first light transmission adjustment unit 333a to reach the protective film 990.

The first lens unit 335a may be located between the first light transmission adjustment layer 333a and the first side surface 900a of the multilayer structure 900. The first lens unit 333a may convert the light of the first color, which transmits through the first light transmission adjustment unit 333a among the light emitted from the first light source unit 331a, into sheet light. Other features of the first lens unit 335a are identical to those of the first lens unit 135 described above with reference to FIGS. 1, 4 and 5, and thus a description thereof will be omitted.

The second light irradiation unit 330b provides light to a second side surface 900b of the multilayer structure 900. The second light irradiation unit 330b provides light to a side surface of any one of the polarizer 930, the resin layer 950, the touch panel 970 and the protective film 990. The second light irradiation unit 330b may be placed to face the second side surface 900b of the multilayer structure 900. The second light irradiation unit 330b may be located on the stage 310 as illustrated in the drawings, but the invention is not limited thereto.

The second light irradiation unit 330b may include a second light source unit 331b, a second light transmission adjustment unit 333b and a second lens unit 335b.

The second light source unit 331b outputs light of a second color toward the second side surface 900b of the multilayer structure 900. In some exemplary embodiments, the light of the second color may be different in color from the light of the first color emitted from the first light source unit 331a. In some exemplary embodiments, the second light source unit 331b may include a laser or LED that generates and emits light.

The second light transmission adjustment unit 333b transmits only part of the light of the second color emitted from the second light source unit 331b. The second light transmission adjustment unit 333b may be located between the second side surface 900b of the multilayer structure 900 and the second light source unit 331b.

The second light transmission adjustment unit 333b may include a second hole Hb defined therein, and the second hole Hb may be located at a position corresponding to the touch panel 970 of the multilayer structure 900. That is, light emitted from the second light source unit 331b may pass through the second hole Hb of the second light transmission adjustment unit 333b to reach the touch panel 970.

The second lens unit 335b may be located between the second light transmission adjustment unit 333b and the second side surface 900b of the multilayer structure 900. Other features of the second lens unit 335b are identical to those of the first lens unit 135 described above with reference to FIGS. 1, 4 and 5, and thus a description thereof will be omitted.

The third light irradiation unit 330c, like the first light irradiation unit 330a and the second light irradiation unit 330b, provides light to a third side surface 900c of the multilayer structure 900. The third light irradiation unit 330c may be placed to face the third side surface 900c of the multilayer structure 900.

The third light irradiation unit 330c may include a third light source unit 331c, a third light transmission adjustment unit 333c and a third lens unit 335c.

The third light source unit 331c outputs light of a third color toward the third side surface 900c of the multilayer structure 900. In some exemplary embodiments, the light of the third color may be different in color from the light of the first color and the light of the second color. In some exemplary embodiments, the third light source unit 331c may include a laser or LED that generates and emits light.

The third light transmission adjustment unit 333c transmits only part of the light of the third color emitted from the third light source unit 331c. The third light transmission adjustment unit 333c may be located between the third side surface 900c of the multilayer structure 900 and the third light source unit 331c.

The third light transmission adjustment unit 333c may include a third hole Hc defined therein, and the third hole Hc may be located at a position corresponding to the resin layer 950 of the multilayer structure 900. That is, light emitted from the third light source unit 331c may pass through the third hole Hc of the third light transmission adjustment unit 333c to reach the resin layer 950.

The third lens unit 335c may be located between the third light transmission adjustment unit 333c and the third side surface 900c of the multilayer structure 900. Other features of the third lens unit 335c are identical to those of the first lens unit 135 described above with reference to FIGS. 1, 4 and 5, and thus a description thereof will be omitted.

The fourth light irradiation unit 330d provides light to a fourth side surface 900d of the multilayer structure 900. The fourth light irradiation unit 330d may be placed to face the fourth side surface 900d of the multilayer structure 900.

The fourth light irradiation unit 330d may include a fourth light source unit 331d, a fourth light transmission adjustment unit 333d and a fourth lens unit 335d.

The fourth light source unit 331d outputs light of a fourth color toward the fourth side surface 900d of the multilayer structure 900. In some exemplary embodiments, the light of the fourth color may be different in color from the light of the first color, the light of the second color and the light of the third color. In some exemplary embodiments, the fourth light source unit 331d may include a laser or LED that generates and emits light.

The fourth light transmission adjustment unit 333d transmits only part of the light of the fourth color emitted from the fourth light source unit 331d. The fourth light transmission adjustment unit 333d may be located between the fourth side surface 900d of the multilayer structure 900 and the fourth light source unit 331d.

The fourth light transmission adjustment unit 333d may include a fourth hole Hd defined therein, and the fourth hole Hd may be located at a position corresponding to the polarizer 930 of the multilayer structure 900. That is, light emitted from the fourth light source unit 331d may pass through the fourth hole Hd of the fourth light transmission adjustment unit 333d to reach the polarizer 930.

The fourth lens unit 335d may be located between the fourth light transmission adjustment unit 333d and the fourth side surface 900d of the multilayer structure 900. Other features of the fourth lens unit 335d are identical to those of the first lens unit 135 described above with reference to FIGS. 1, 4 and 5, and thus a description thereof will be omitted.

The image capture unit 350 obtains image information by receiving light (or scattered light) generated when light irradiated from each of the first through fourth light irradiation units 330a through 330d is scattered by a foreign body existing within the multilayer structure 900. In some exemplary embodiments, the image capture unit 350 may obtain color image information (or a color image) by receiving scattered light. To this end, the image capture unit 350 may include, but not limited to, a CCD or a CMOS.

The control unit 370 detects foreign body information of the multilayer structure 900 based on image information obtained by the image capture unit 350. In some exemplary embodiments, the control unit 370 may detect the foreign body information based on at least one (in particular, color information) of color, chroma, and light and shade included in the image information. In addition, the control unit 370 may store the color information of light provided to each layer of the multilayer structure 900 and determine in which layer of the multilayer structure 900 a foreign body exists based on the color information. Furthermore, the control unit 370 may control the overall operation of the inspecting apparatus 30. In an exemplary embodiment, the control unit 370 may control the driving timing of the light source unit 331a, 331b, 331c or 331d included in each of the first through fourth light irradiation units 330a through 330d. One or more of the first through fourth light irradiation units 330a through 330d may be driven to provide light simultaneously, or each of the first through fourth light irradiation units 330a through 330d may be driven separately.

Figure 14:
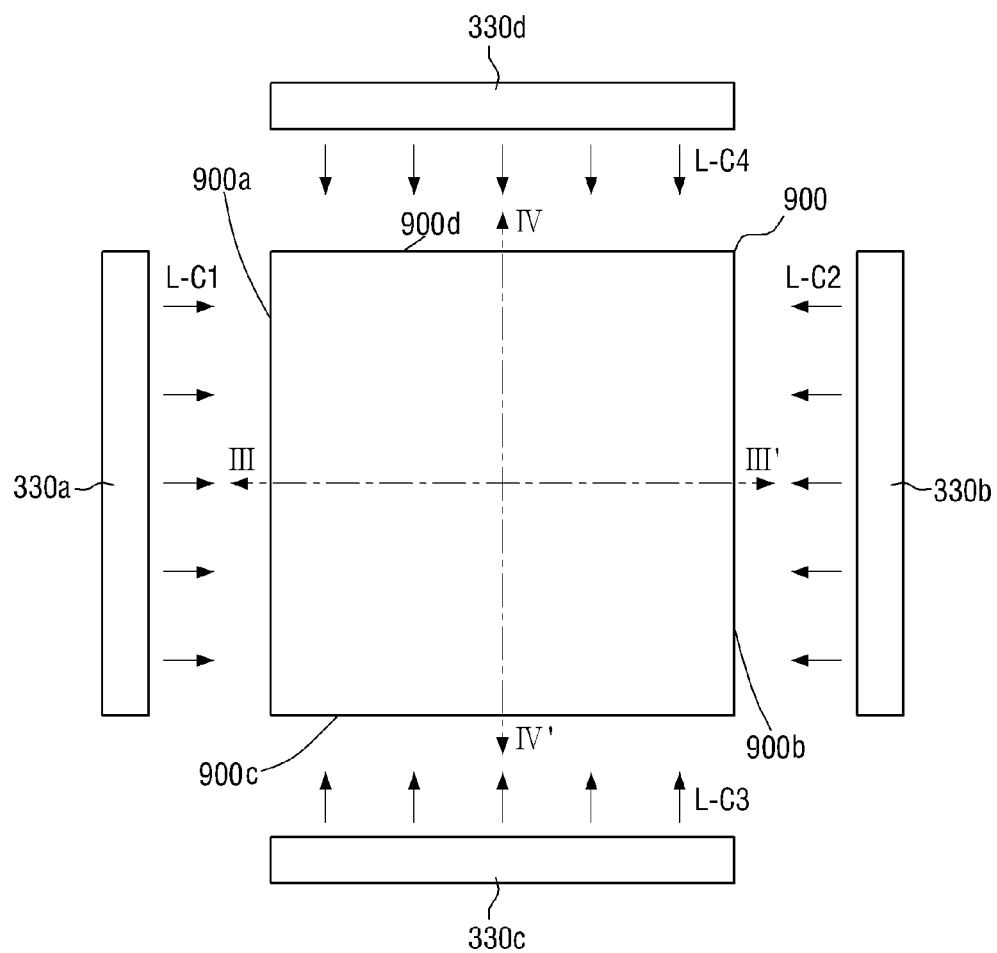
Figure 15:
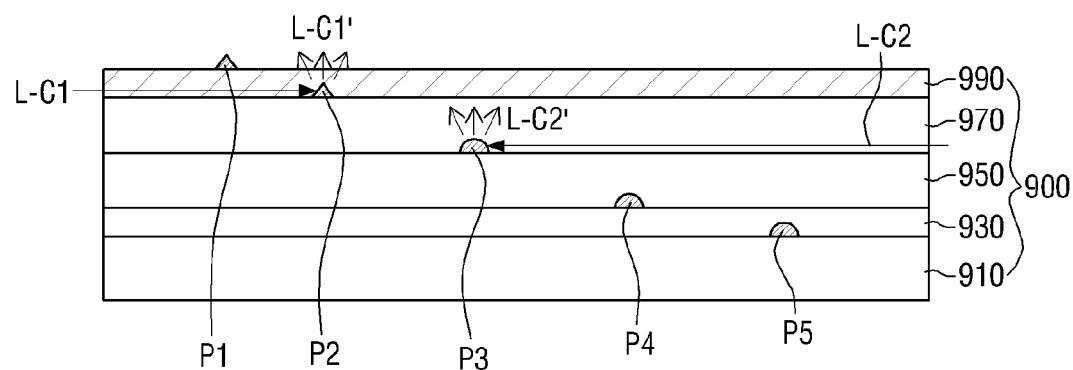
Figure 16:
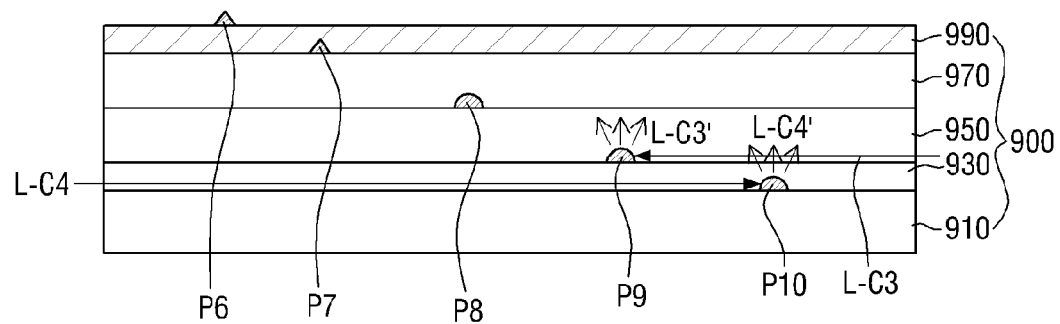

FIGS. 14 through 16 are diagrams illustrating an exemplary embodiment of a process of detecting foreign bodies using the inspecting apparatus 30 of FIG. 11. More specifically, FIG. 14 is a plan view of the inspecting apparatus 30 by which light is provided to the multilayer structure 900, FIG. 15 is a cross-sectional view taken along the line III-III' of FIG. 14, and FIG. 16 is a cross-sectional view taken along the line IV-IV' of FIG. 14.

A multilayer structure 900 including first through tenth foreign bodies P1 through P10 will now be described as an example with reference to FIGS. 12 through 16. In addition, it will be assumed that the first through fifth foreign bodies P1 through P5 are located on the line III-III' and that the sixth through tenth foreign bodies P6 through P10 are located on the line IV-IV'.

Referring to FIGS. 12 through 16, the inspecting apparatus 30 simultaneously drives the first light source unit 331a, the second light source unit 331b, the third light source unit 331c and the fourth light source unit 331d to emit light L-C1 of a first color, light L-C2 of a second color, light L-C3 of a third color, and light L-C4 of a fourth color.

The light L-C1 of the first color passes through the first hole Ha to reach the first lens unit 335a. As the light L-C1 of the first color transmits through the first lens unit 335a, the transmitted light is transformed into sheet light and then proceeds toward the first side surface 900a of the multilayer structure 900 to be incident upon a side surface of the protective film 990.

The light L-C2 of the second color passes through the second hole Hb to reach the second lens unit 335b. As the light L-C2 of the second color transmits through the second lens unit 335b, the transmitted light is transformed into sheet light and then proceeds toward the second side surface 900b of the multilayer structure 900 to be incident upon a side surface of the touch panel 970.

The light L-C3 of the third color passes through the third hole Hc to reach the third lens unit 335c. As the light L-C3 of the third color transmits through the third lens unit 335c, the transmitted light is transformed into sheet light and then proceeds toward the third side surface 900c of the multilayer structure 900 to be incident upon a side surface of the resin layer 950.

The light L-C4 of the fourth color passes through the fourth hole Hd to reach the fourth lens unit 335d. As the light L-C4 of the fourth color transmits through the fourth lens unit 335d, the transmitted light is transformed into sheet light and then proceeds toward the fourth side surface 900d of the multilayer structure 900 to be incident upon a side surface of the polarizer 930.

The light L-C1 of the first color entering the protective film 990 of the multilayer structure 900 is scattered by the second foreign body P2 to generate scattered light L-C1' of the first color and is scattered by the seventh foreign body P7 to generate scattered light of the first color (not illustrated). In addition, the light L-C2 of the second color entering the touch panel 970 of the multilayer structure 900 is scattered by the third foreign body P3 to generate scattered light L-C2' of the second color and is scattered by the eighth foreign body P8 to generate scattered light of the second color (not illustrated). Similarly, the light L-C3 of the third color entering the resin layer 950 of the multilayer structure 900 is scattered by the fourth foreign body P4 to generate scattered light of the third color (not illustrated) and is scattered by the ninth foreign body P9 to generate scattered light L-C3' of the third color. Likewise, the light L-C4 of the fourth color entering the polarizer 930 of the multilayer structure 900 is scattered by the fifth foreign body P5 to generate scattered light of the fourth color (not illustrated) and is scattered by the tenth foreign body P10 to generate scattered light L-C4' of the fourth color.

The image capture unit 350 obtains color image information by receiving the scattered light L-C1' of the first color, the scattered light L-C2' of the second color, the scattered light L-C3' of the third color, and the scattered light L-C4' of the fourth color. The control unit 370 determines whether a foreign body exists in the multilayer structure 900 by analyzing the color image information obtained by the image capture unit 350.

In an exemplary embodiment, the light L-C1 of the first color may be red light, the light L-C2 of the second color may be green light, the light L-C3 of the third color may be blue light and the light L-C4 of the fourth color may be yellow light. Here, in the color image information, portions corresponding to the second foreign body P2 and the seventh foreign body P7 may be displayed as red dots, portions corresponding to the third foreign body P3 and the eighth foreign body P8 may be displayed as green dots, portions corresponding to the fourth foreign body P4 and the ninth foreign body P9 may be displayed as blue dots, and portions corresponding to the fifth foreign body P5 and the tenth foreign body P10 may be displayed as yellow dots. By analyzing the color image information, the control unit 370 may detect whether the second foreign body P2, the third foreign body P3, the fourth foreign body P4, the fifth foreign body P5, the seventh foreign body P7, the eighth foreign body P8, the ninth foreign body P9 and the tenth foreign body P10 exist. In addition, the control unit 370 may detect in which layer of the multilayer structure 900 each of the second foreign body P2, the third foreign body P3, the fourth foreign body P4, the fifth foreign body P5, the seventh foreign body P7, the eighth foreign body P8, the ninth foreign body P9 and the tenth foreign body P10 is located based on the stored color information of light provided to each layer of the multilayer structure 900.

That is, since the control unit 370 can detect the presence and position of each of the foreign bodies P2 through P5 and P7 through P10, a single one inspection process can be used to detect whether defects actually exist within the multilayer structure 900.

In an exemplary embodiment, for example, the first foreign body P1, the second foreign body P2, the sixth foreign body P6 and the seventh foreign body P7 can be removed when the protective film 990 is stripped off during a subsequent manufacturing process of a display including the multilayer structure 900. Therefore, despite the presence of the second foreign body P2 or the seventh foreign body P7, the control unit 370 may not determine the second foreign body P2 or the seventh foreign body P7 to be a foreign body defect. On the other hand, the control unit 370 may determine the third foreign body P3, the fourth foreign body P4, the fifth foreign body P5, the eighth foreign body P8, the ninth foreign body P9 and the tenth foreign body P10 to be foreign body defects.

According to the exemplary embodiment of the invention, not only the presence of a foreign body in the multilayer structure 900 but also the position of the foreign body can be detected. Therefore, accurate detection of whether a foreign body defect actually exists in the multilayer structure 900 and the position of the foreign body within the multilayer structure 900 is possible. Furthermore, since foreign body defects within the multilayer structure 900 can be detected through one single inspection process, an additional advantage of reducing inspection time can be provided.

One or more exemplary embodiment of the invention provides at least one of the following advantages.

According to one or more exemplary embodiment of the invention, a defect in a multilayer structure can be detected more effectively.

However, the advantages and effects of the invention are not restricted to those set forth herein. The above and other effects of the invention will become more apparent to one of daily skill in the art to which the invention pertains by referencing the claims.

While the invention has been particularly shown and described with reference to exemplary embodiments thereof, it will be understood by those of ordinary skill in the art that various changes in form and detail may be made therein without departing from the spirit and scope of the invention as defined by the following claims. The exemplary embodiments should be considered in a descriptive sense only and not for purposes of limitation.

What is claimed is:

1. An inspecting apparatus comprising:
   a stage comprising a top surface on which a multilayer structure comprising a first layer and a second layer in different planes along a thickness direction of the multilayer structure is placed;
   a first light irradiator which faces a first side surface of the multilayer structure and comprises:
      a first light source which generates light and is extended to simultaneously emit the light in the different planes along the thickness direction of the multilayer structure,
      wherein
      for the first and second layers in different planes along the thickness of the multilayer structure, the first light irradiator selectively provides the light from the first light source to one among a plane in which a first side surface of the first layer is disposed and a plane in which a first side surface of the second layer is disposed, and
      the light provided to the multilayer structure is scattered therein to generate scattered light;
   an image detector which is on the multilayer structure placed on the stage, receives the scattered light from the multilayer structure and generates image information of the multilayer structure from the received scattered light; and
   a controller which is connected to the image detector and configured to determine foreign body information of the multilayer structure from the image information of the multilayer structure which is generated by the image detector.

2. The inspecting apparatus of claim 1, wherein the first light irradiator further comprises:
   a first light transmission adjuster which is between the first light source and the first side surface of the multilayer structure, and comprises:
      a first shutter at a position corresponding to the plane in which the first side surface of the first layer is disposed and adjusts transmission of the light from the first light source to the plane in which the first side surface of the first layer is disposed, and
      a second shutter at a position corresponding to the plane in which the first side surface of the second layer is disposed and adjusts transmission of the light from the first light source to the plane in which the first side surface of the second layer is disposed.

3. The inspecting apparatus of claim 2, wherein the controller is further configured to control the first shutter and the second shutter to open at different times.

4. The inspecting apparatus of claim 2, wherein the first light irradiator further comprises a first lens which is between the first light transmission adjuster and the first side surface of the multilayer structure and converts light transmitted through the first light transmission adjuster into sheet light.

5. The inspecting apparatus of claim 1, further comprising a second light radiator which faces a second side surface of the multilayer structure and comprises a second light source which generates light and is extended to simultaneously emit the light in the different planes along the thickness direction of the multilayer structure,
wherein for the first and second layers in the different planes along the thickness of the multilayer structure, the second light irradiator selectively provides the light from the second light source to one among a plane in which a second side surface of the first layer is disposed or a plane in which a second side surface of the second layer is disposed.

6. The inspecting apparatus of claim 5, wherein the second light irradiator comprises:
a second light transmission adjuster which is between the second light source and the second side surface of the multilayer structure, and comprises:
a first shutter which is at a position corresponding to the plane in which the second side surface of the first layer is disposed and adjusts transmission of the light from the second light source to the plane in which the second side surface of the first layer is disposed, and
a second shutter which is at a position corresponding to the plane in which the second side surface of the second layer is disposed and adjusts transmission of the light from the second light source to the plane in which the second side surface of the second layer is disposed.

7. An inspecting apparatus comprising:
a stage comprising a top surface on which a multilayer structure comprising a first layer and a second layer in different planes along a thickness direction of the multilayer structure is placed;
a first light irradiator which faces a first side surface of the multilayer structure and comprises:
a first light source which generates a light which is converted to color light and is extended to simultaneously emit the light in the different planes along the thickness direction of the multilayer structure, wherein for the first and second layer in different planes along the thickness of the multilayer structure, the first light irradiator provides light of a first color to a plane in which a first side surface of the first layer is disposed, and provides light of a second color to a plane in which a first side surface of the second layer is disposed, and
the light of the first color and the light of the second color provided to the multilayer structure is scattered therein to generate scattered light comprising the light of the first color or the light of the second color;
an image detector which is on the multilayer structure placed on the stage, receives the scattered light from the multilayer structure and generates image information of the multilayer structure from the scattered light; and
a controller which is connected to the image detector and configured to determine foreign body information of the multilayer structure from the image information of the multilayer structure which is generated by the image detector.

8. The inspecting apparatus of claim 7, wherein the first light irradiator comprises:
a first light converter which is between the first light source and the first side surface of the multilayer structure, and comprises:
a first light sub-converter which converts the light emitted from the first light source into the light of the first color and provides the light of the first color to the plane in which the first side surface of the first layer is disposed, and
a second light sub-converter which converts the light emitted from the first light source into the light of the second color and provides the light of the second color to the plane in which the first side surface of the second layer is disposed.

9. The inspecting apparatus of claim 8, wherein
the first light sub-converter is a first color filter, and
the second light sub-converter is a second color filter different in color from the first color filter.

10. The inspecting apparatus of claim 8, wherein the first light source emits white light.

11. The inspecting apparatus of claim 8, wherein
the multilayer structure further comprises a third layer in a plane different from that of the first or second layer,
the first light source emits the light toward a first side surface of the third layer,
the first light converter further comprises a third light sub-converter which converts the light emitted from the first light source into light of a third color and provides the light of the third color to the plane in which the first side surface of the third layer is disposed, and
the light of the third color is different in color from the light of the first color and the light of the second color.

12. The inspecting apparatus of claim 8, wherein the first light irradiator further comprises a first lens which is between the first light converter and the first side surface of the multilayer structure and converts the light of the first color or the light of the second color output from the first light converter into sheet light.

13. An inspecting apparatus comprising:
a stage comprising a top surface on which a multilayer structure comprising a first layer and a second layer in different planes along a thickness direction of the multilayer structure is placed;
a first light irradiator which faces a first side surface of the multilayer structure and comprises a first light source which generates light of a first color and is extended to simultaneously emit the light of the first color in the different planes along the thickness direction of the multilayer structure,
wherein for the first and second layers in different planes along the thickness of the multilayer structure, the first light irradiator selectively provides the light of the first color from the first light source to a plane in which a first side surface of the first layer is disposed;
a second light irradiator which faces a second side surface of the multilayer structure different from the first side surface, and comprises a second light source which generates light of a second color and is extended to simultaneously emit the light of the second color in the different planes along the thickness direction of the multilayer structure,
wherein for the first and second layers in different planes along the thickness of the multilayer structure, the second light irradiator selectively provides the light of the second color from the second light source to a plane in which a second side surface of the second layer is disposed, wherein the light of the first color and the light of the second color provided to the multilayer structure is scattered therein to generate scattered light comprising the light of the first color or the light of the second color;

an image detector which is on the multilayer structured placed on the stage, receives the scattered light from the multilayer structure and generates image information of the multilayer structure from the received scattered light; and a controller which is connected to the image detector and configured to determine foreign body information of the multilayer structure from the image information of the multilayer structure which is generated by the image detector.

14. The inspecting apparatus of claim 13, wherein the first light irradiator comprises:

a first light transmission adjuster which is between the first light source and the first side surface of the multilayer structure, and comprises:

a first hole defined therein corresponding to the plane in which the first layer is disposed and through which the light of the first color is emitted toward the first side surface of the multilayer structure to adjust transmission of the light from the first light source to the plane in which the first side surface of the first layer is disposed.

15. The inspecting apparatus of claim 14, wherein the first light irradiator further comprises a first lens which is between the first light transmission adjuster and the first side surface of the multilayer structure and converts the light of the first color transmitted through the first light transmission adjuster into sheet light.

16. The inspecting apparatus of claim 14, wherein the second light irradiator comprises:

a second light transmission adjuster which is between the second light source and the second side surface of the multilayer structure, and comprises:

a second hole defined therein corresponding to the plane in which the second layer is disposed and through which the light of the second color is emitted toward the second side surface of the multilayer structure to adjust transmission of the light from the second light source to the plane in which the second side surface of the second layer is disposed.

17. The inspecting apparatus of claim 16, wherein the second light irradiator further comprises a second lens which is between the second light transmission adjuster and the second side surface of the multilayer structure and converts the light of the second color transmitted through the second light transmission adjuster into sheet light.

18. The inspecting apparatus of claim 13, wherein the controller is further configured to control the first light irradiator and the second light irradiator to simultaneously provide the light of the first color and the light of the second color to the different planes along the thickness direction of the multilayer structure.

19. The inspecting apparatus of claim 13, wherein the light of the first color and the light of the second color are different in color from each other.

20. The inspecting apparatus of claim 13, wherein the multilayer structure further comprises a third layer in a plane different from that of the first or second layer, further comprising a third light irradiator which faces a third side surface of the multilayer structure and comprises a third light source which generates light of a third color and is extended to simultaneously emit the light of the third color in the different planes along the thickness direction of the multilayer structure, wherein for the first, second and third layers in different planes along the thickness of the multilayer structure, the third light irradiator selectively provides the light of the third color to a plane in which a third side surface of the third layer is disposed, wherein the light of the third color different in color from the light of the first color and the light of the second color.

* * * * *